(12) United States Patent
Brown (10) Patent No.: US 7,740,595 B2
(45) Date of Patent: Jun. 22, 2010

(54) TISSUE AND FLUID SAMPLING DEVICE

(76) Inventor: Stuart Brown, 66 Taylor St., Needham, MA (US) 02494

(*) Notice: Subject to any disclaimer, the term of this patent is extended or adjusted under 35 U.S.C. 154(b) by 516 days.

(21) Appl. No.: 10/629,048

(22) Filed: Jul. 28, 2003

(65) Prior Publication Data

US 2004/0024333 A1 Feb. 5, 2004

Related U.S. Application Data

(60) Provisional application No. 60/398,963, filed on Jul. 26, 2002.

(51) Int. Cl.
*A61B 10/00* (2006.01)
(52) U.S. Cl. ........................ 600/565; 600/566
(58) Field of Classification Search ................ 600/564, 600/562, 565, 566, 567
See application file for complete search history.

(56) References Cited

U.S. PATENT DOCUMENTS

| | | | | |
|---|---|---|---|---|
| 4,305,406 A | * | 12/1981 | Megahed | 600/579 |
| 5,285,795 A | * | 2/1994 | Ryan et al. | 600/563 |
| 5,295,990 A | * | 3/1994 | Levin | 606/49 |
| 5,320,627 A | | 6/1994 | Sorensen et al. | 606/128 |
| 5,372,124 A | * | 12/1994 | Takayama et al. | 600/106 |
| 5,415,182 A | * | 5/1995 | Chin et al. | 600/567 |
| 5,526,822 A | | 6/1996 | Burbank et al. | 128/754 |
| 5,531,756 A | * | 7/1996 | Larose | 606/184 |
| 5,562,102 A | | 10/1996 | Taylor | |
| 5,595,185 A | | 1/1997 | Erlich | |
| 5,649,547 A | | 7/1997 | Ritchart et al. | |
| 5,785,044 A | | 7/1998 | Meador et al. | |
| 5,794,626 A | * | 8/1998 | Kieturakis | 600/567 |
| 5,810,744 A | | 9/1998 | Chu et al. | |
| 5,827,305 A | | 10/1998 | Gordon | |
| 5,840,044 A | | 11/1998 | Dassa et al. | |
| 5,871,453 A | | 2/1999 | Banik et al. | |
| 5,928,161 A | * | 7/1999 | Krulevitch et al. | 600/564 |
| 6,019,733 A | | 2/2000 | Farascioni | |
| 6,050,138 A | | 4/2000 | Lynch et al. | |
| 6,050,955 A | | 4/2000 | Bryan et al. | |
| 6,053,877 A | | 4/2000 | Banik et al. | |
| 6,071,248 A | | 6/2000 | Zimmon | |
| 6,083,150 A | | 7/2000 | Aznoian et al. | |

(Continued)

FOREIGN PATENT DOCUMENTS

WO WO 97/24070 7/1997

(Continued)

OTHER PUBLICATIONS

International Search Report for PCT/US03/23551, mailed Nov. 26, 2003.

*Primary Examiner*—Max Hindenburg
*Assistant Examiner*—Michael C Stout
(74) *Attorney, Agent, or Firm*—Mintz, Levin, Cohn, Ferris, Glovsky and Popeo, P.C.

(57) ABSTRACT

An instrument for removing a tissue sample from a subject comprises a plurality of tissue sampling devices having respective chambers, the tissue sampling devices being radially disposed along a length of the instrument such that upon insertion of the instrument into the subject one or more samples are extracted and isolated in the respective chambers of the sampling devices at the site at which removal occurs.

24 Claims, 4 Drawing Sheets

U.S. PATENT DOCUMENTS

| | | | |
|---|---|---|---|
| 6,110,129 A | 8/2000 | Terwilliger | |
| 6,142,957 A | 11/2000 | Diamond et al. | |
| 6,280,450 B1 * | 8/2001 | McGuckin, Jr. | 606/114 |
| 6,419,640 B1 | 7/2002 | Taylor | |
| 6,428,486 B2 | 8/2002 | Ritchart et al. | |
| 6,485,436 B1 | 11/2002 | Truckai et al. | |
| 6,488,636 B2 | 12/2002 | Bryan et al. | |
| 6,530,891 B2 | 3/2003 | Miller | |
| 6,695,787 B2 * | 2/2004 | Hogendijk et al. | 600/463 |
| 2002/0193705 A1 * | 12/2002 | Burbank et al. | 600/562 |
| 2004/0236211 A1 * | 11/2004 | Burbank et al. | 600/431 |

FOREIGN PATENT DOCUMENTS

| | | |
|---|---|---|
| WO | WO 99/07288 | 2/1999 |
| WO | WO 99/20096 | 4/1999 |
| WO | WO 00/44285 | 8/2000 |
| WO | WO 01/52742 | 7/2001 |
| WO | WO 01/82998 A2 | 11/2001 |
| WO | WO 02/062228 A1 | 8/2002 |
| WO | WO 02/062229 | 8/2002 |
| WO | WO 02/062231 | 8/2002 |

* cited by examiner

TISSUE AND FLUID SAMPLING DEVICE

CLAIM OF PRIORITY TO PRIOR APPLICATIONS

This application claims priority under 35 U.S.C. §119(e) to U.S. provisional patent application Ser. No. 60/398,963, filed on Jul. 26, 2002, which is incorporated herein by reference.

FIELD OF THE INVENTION

The invention is related to medical instrumentation, and more particularly to the rapid, minimally invasive collection of multiple tissue and fluid samples.

BACKGROUND OF THE INVENTION

Fluid and tissue sampling is used in a number of fields, including gastroenterology, cardiology, oncology, radiology, ophthalmology, histology, neurology and neurosurgery, internal medicine, and renal specialties. Fluid and tissue samples are necessary for a number of purposes in the medical arena, including in the performance of biopsies, or the removal of tissue samples. Removed tissue from a patient is often used in diagnosis of, for example, a variety of diseases. Often, to make an accurate diagnosis, a number of tissue samples are necessary, as a single tissue sample can fail to represent the entirety of the area, organ, or lesion from which the sample is extracted. Taking a plurality of samples can be not only time consuming, but it can expose the patient to additional and repeated discomfort.

Tissue samples are extracted from a patient according to a variety of devices, including manually or automatically controlled needle devices, cutting jaw devices, and with catheters having cutting devices disposed on one end, for example. It is desirable to extract a number of tissue samples in a minimally invasive manner.

SUMMARY OF THE INVENTION

The invention provides apparatus and methods for collecting multiple tissue samples and fluid samples in a rapid and substantially minimally invasive manner. Microminiature manufacturing technologies are used to produce a biopsy and/or fluid sampling device. In certain embodiments of the invention, a sampling platform or apparatus such as a biopsy catheter, includes multiple sampling devices that can take many samples without the withdrawal and reinsertion of multiple catheters. The multiple sampling devices are positioned along the outer diameter of the shaft portion of a single catheter or other device, and samples are collected and stored in respective chambers of the sampling devices, alleviating the need to transport the samples to distal locations.

Accordingly, the invention features an instrument for removing a tissue sample from a subject containing a housing, which contains a plurality of independently-controlled tissue sampling devices, each of the devices containing an isolated chamber. By "isolated" is meant that the chamber is physically and spatially separated from another chamber. The chamber is closed to an interior lumen of the housing. The lumen may be used to provide actuation to the sampling devices. Once a tissue sample is removed from an anatomical site adjacent to the chamber, the chamber is sealed. Each chamber is integral to the instrument and acts as a self-contained storage unit, i.e., tissue is not transported to an off-site storage compartment, but remains in the chamber until the device is removed from the subject. The volume of the chamber is preferably less than 1.2 cubic millimeters, e.g., the volume ranges from 0.001 to 1 cubic millimeters. In preferred embodiments the volume is 0.005, 0.01, 0.05, 0.1, 0.5, 0.75 cubic millimeters.

The housing in which the sampling devices are located is hollow or solid. In the former case, the housing contains an interior lumen. The lumen optionally contains a deployment control element for deploying one or more of the sampling devices. The sampling devices are deployed by contacting the device with an actuation signal emitted by the element. For example, the deployment control element emits an electrical, optical, pneumatic, hydraulic, RF- transmitted, inductive, magnetic, thermal or sonic signal, which mediates opening of the chamber and/or deployment of the sampling device to obtain a tissue sample from the subject. The chamber does not communicate the tissue sample to the interior lumen of the instrument, and once the chamber is sealed, tissue sample is not communicated to the outside or to any other chamber, thereby avoiding cross-contamination between samples and loss of sample in transport to a distal sample storage facility. In the case of a solid housing, the deployment control device is embedded in or located on an exterior surface of the housing. For example, a wire runs along the outside of the housing and makes contact with each sampling device/chamber assembly. In either configuration, signal is applied to one of more sampling device simultaneously or sequentially to sample tissues from spatially distinct anatomic locations.

The tissue sampling devices are radially and longitudinally disposed about the instrument such that upon insertion of the instrument into the subject one or more samples are extracted and isolated in the respective chambers of the sampling devices at the site at which removal occurs. For example, the tissue sampling devices are positioned in an array along the length of the instrument. Alternatively, the tissue sampling devices are fixed in a position along an outside diameter of an exterior face of the instrument.

Tissue samples are removed from a bodily tissue using a variety of methods such as scraping or cutting using a jaw or knife mechanism. For example, each sampling device optionally contains a set of jaws activated by an expandable volume to mechanically actuate and collect a sample. The tissue sampling devices include vacuum sampling chambers, which pull tissue into the chamber. The vacuum sampling chambers are characterized by a pressure differential, e.g., a lower pressure, compared to surrounding tissues. When the chamber is opened, tissue is automatically drawn into the chamber. In another example, the tissue sampling devices includes a mechanical cutting sampling device such as a sleeve containing a knife edge. The sleeve is located exterior to the chambers and is slidably disposed over the housing. The sleeve optionally includes a sealing element. Following cutting of a tissue sample and deposition of the sample in the chamber, the sleeve seals the chamber, e.g., by mechanical closure or application of heat to a bonding material.

Also within the invention is a plurality of tissue sampling devices positioned on a catheter or needle for abstracting at least one tissue sample from a living subject. Each sampling device in the plurality contains a chamber with a cover, which is closed by means of a bonding material. Opening and closing of the chamber is controlled by application of a vacuum or other force that compromises the integrity of the bonding material. The cover is a single unit or contains two sides, which meet and close the chamber by means of bonding material such as an adhesive or a conductive polymer. The vacuum draws tissue into the chamber as the bonding material separates causing a separation of the two sides of the cover. The chamber is comprised of at least one of the group consisting of silicon, biodegradable polymer, metal, and a metal alloy. The chamber is opened by applying a stress force to the bonding material, which leads to release of the cover. For example, the two sides of the cover separate when a temperature differential is applied to a bonding material connecting the two sides of the cover. In the case of a single unit chamber cover, the cover segment mechanically actuates or opens to allow deposition of a tissue sample upon application of heat to the cover.

Tissue sampling devices are equipped with a means to extract a sample from a bodily tissue. For example, the device contains a three-dimensional scoop to remove tissue from a subject. The scoop includes a cutting edge to remove a tissue sample and is pivotally connected to the instrument such that the scoop is pivotally activated to collect the tissue sample and carry the sample as the scoop pivots to a position in which the tissue sample is deposited in a chamber and the scoop is at a resting position. In another example, the sampling device includes a chamber having a set of jaws disposed therein. The set of jaws extends from the chamber to collect a sample when the set of jaws are mechanically activated. After the sample is obtained, the jaws are retracted, and the sample is deposited and retained in the chamber. The chamber further optionally contains a heating element and an expandable volume, and the heating element causes the expandable volume to expand to actively deploy the set of jaws for collection of the sample.

The invention also includes a method of extracting multiple tissue samples from a subject by inserting into the subject an instrument with a plurality of independently-controlled tissue sampling devices on a housing, each of which contains an isolated chamber. The sampling device is contacted with a deployment signal, e.g., an electrical, optical, pneumatic, RF-transmitted, inductive, magnetic, thermal or sonic signal, which leads to an opening of the chamber. Following opening of the chamber, a tissue sample is removed from an anatomical location adjacent to the chamber and the chamber sealed. The tissue extraction element and sealing element are optionally disposed on a sleeve that slides along the length of the instrument. The sampling devices are deployed simultaneously or temporally. For example, the sampling devices are deployed sequentially at minute, second, or millisecond intervals. Alternatively, the devices are deployed at selected spatial locations together or in sequence. Sampling is controlled in real time by the operator (e.g., based on information from an imaging device regarding the position of the instrument relative to the location of a target tissue) or by means of a predetermined program, e.g., a computer controlled sampling program.

An alternative method includes the steps of inserting the instrument into the subject; heating the plurality of sampling devices (heating causing actuation of a mechanical portion of the plurality of sampling devices, such that a mechanical portion of the sampling devices collects a sample and retains the sample); depositing the sample into a local chamber; and, removing the instrument from the subject. Heating is accomplished by passing electrical current through a portion of the extracting device. Collecting and retaining the sample is accomplished by applying a differential pressure to the local chamber and sucking the sample into the local chamber. Samples are ejected by pressurizing the chamber. Alternatively, collection and retention of the sample is carried out by scooping the sample from the subject by pivoting a scoop from a rest position after heating the scoop. In yet another example, collecting and retaining the sample is carried out by expanding a volume of a fluid in a chamber and causing a set of jaws to deploy from the chamber. Positioning the instrument and locating target tissues to be sampled is accomplished by a variety of imaging techniques, e.g., fiberoptically or by magnetic resonance imaging (MRI). In the former case, the instrument contains a fiberoptic imaging device.

Implementations of the invention may include one or more of the following features. A plurality of miniature biopsy sampling devices are included on a single catheter. A single catheter includes 2, 5, 10, 20, 50, and up to hundreds of miniature sampling devices. Still further embodiments of the invention can include less than about 5 miniature biopsy sampling devices on a single catheter, while still other embodiments include greater than about 50 miniature biopsy sampling devices on a single catheter.

The biopsy sampling devices are positioned along the length of the catheter and on an outside diameter of the catheter. The sampling devices remain in position on the outside diameter of the catheter for the duration of insertion of the catheter, collection of the sample, and removal of the sample from the subject. Samples are retained in chambers positioned at the site of sampling, and the chambers sealed for removal of the catheter from the subject. Sampling devices can create a substantially uniform array along the length of the catheter or other instrumentation. The plurality of sampling devices are activated simultaneously such that multiple samples are achieved simultaneously. The sampling devices are alternatively activated individually at the operator's discretion.

Further implementations of the invention may include one or more of the following features. The invention permits the analysis and examination of tissue and/or fluid samples. For example, the analysis and examination of smaller tissue and/or fluid samples reduce the amount of tissue required per analytical procedure. Analytic methods, e.g., Polymerase Chain Reaction (PCR), are used to obtain diagnostic information. The instrumentation and sampling methods described herein permit the replication of genetic data from very small samples, eliminating the need for large tissue samples.

Embodiments of the invention may provide one or more of the following advantages compared to earlier methods. The invention provides devices for use in the sampling of tissue and/or fluids that require fewer sampling procedures to obtain multiple samples. Acquisition of multiple samples is advantageous as it permits a more thorough diagnosis of a particular tissue or physical disorder. Sampling is achieved using insertion of a single device into the subject, which permits a rapid removal procedure and reduces the physical damage associated with the repeated insertion and removal of sampling devices, thus reducing the risk of injury to the patient. The use of a plurality of sampling devices positioned along the perimeter of the catheter provides multiple samples with similar dimensions. The collection of multiple, similarly-sized samples permits the automation of sample analysis, whether chemical, visual, or genomic. In addition, the collection of multiple samples permits the mapping of tissue spatially with a higher resolution or, alternatively, the sampling of tissue or fluids over time with a more accurate evaluation of bodily fluid condition due to a procedure or introduction of a medication. Further, the ability to obtain multiple samples without multiple insertion and removal of sampling devices reduces the sampling time, permitting both shorter procedures and reducing the primary cost of those procedures.

DETAILED DESCRIPTION

The invention utilizes a number of sampling devices that acquire samples of tissue, fluid or other substances in a rapid manner. In one aspect, the invention includes a plurality of miniature sampling devices located on a single sampling platform, such as a catheter. Each of the sampling devices is designed to be sufficiently small to permit the deployment of a plurality of sampling devices on the single, larger apparatus or platform, such as a catheter, that is subsequently inserted into the body. Embodiments of the invention can be used to obtain samples other than tissue or fluid samples, and with apparatus other than catheters. Still other embodiments are within the scope of the invention.

Figure 1:
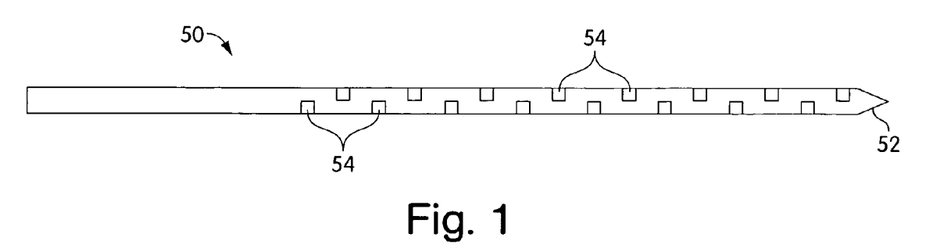
FIG. 1 is a diagram of a catheter employing multiple sampling devices in one embodiment of the invention.

Referring to FIG. 1, a catheter having multiple sampling devices along its length is shown. A catheter is a typical instrument used in the medical arena for insertion into a patient for biopsy or other purposes. The catheter 50 includes a distal insertion end 52 and sampling devices 54. The distal end 52 is a sharp or pointed end that is inserted into the subject requiring removal of tissue or fluid samples. The length of the catheter can vary depending on its intended use. To collect the samples, the catheter employs at least one sampling device 54 that is activated to collect a sample when the catheter is properly inserted. Often, however, collection of a single sample does not provide ample data to make an appropriate diagnosis. Thus, multiple samples are required.

To accomplish extraction of multiple samples, the catheter 50 includes a plurality of sampling devices 54 to take samples with a single insertion of the catheter 50. The sampling devices 54 comprise an array of devices along the length of the catheter 50. The catheter 50 can include any number of sampling devices along its length to complete the array. The devices 54 are positioned on an outside diameter of the catheter 50. The devices remain in a fixed position on the outside diameter of the catheter for insertion, collection, and removal of the catheter 50. Thus, samples collected by the sampling devices 54 are retained in chambers of the sampling devices directly upon being removed from the subject. This alleviates a need to move the samples to a separate portion of the catheter for storage while further samples are collected. Because multiple samples are collected at multiple sites, the catheter 50 can be a solid member, rather than hollow. The catheter may, but need not comprise an inner lumen into which the samples are deposited.

Various sampling devices are used on the catheter 50 to acquire samples. Activation of the sampling devices 54 can occur by methods including, but not limited to, hydraulic activation, electrical activation, and pneumatic activation. Activation can occur using a combination of methods as well. The sampling devices 54 are activated to extract samples simultaneously or separated in time. In addition, the samples can be taken at varying depths in the organ or diseased area. The array of sampling devices 54 is marked to indicate at which level the samples are extracted. The sampling devices 54 allow separation and isolation of the samples collected to avoid cross contamination.

Figure 2:
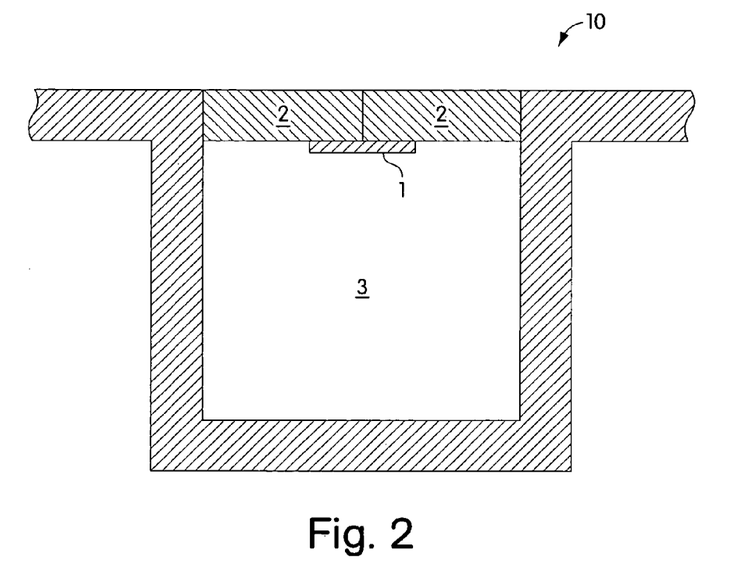
FIG. 2 is a diagram of a vacuum sampling configuration in one embodiment of the invention.
Figure 3:
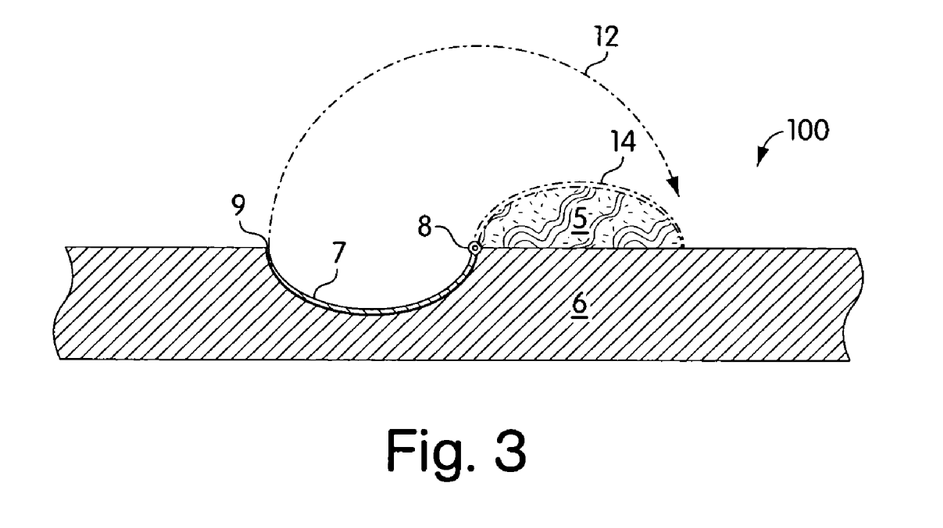
FIG. 3 is a diagram of a mechanical cutting device used in obtaining samples in one embodiment of the invention.
Figure 4A:
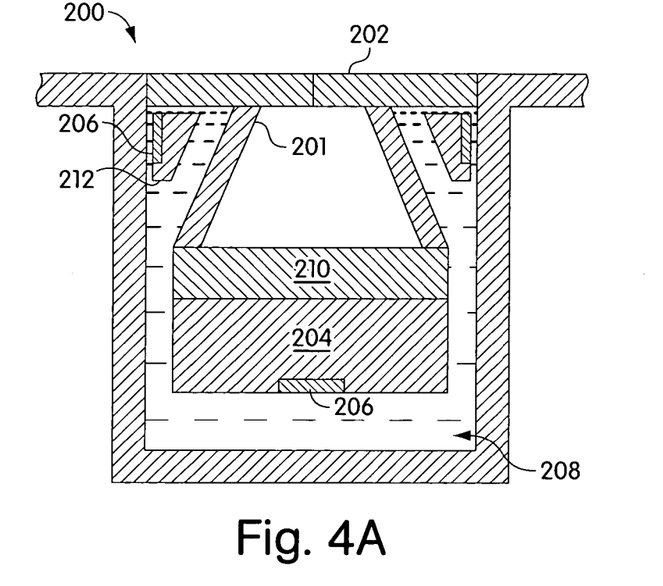
FIG. 4A is a diagram of a sampling device in a position before deployment in one embodiment of the invention.
Figure 4B:
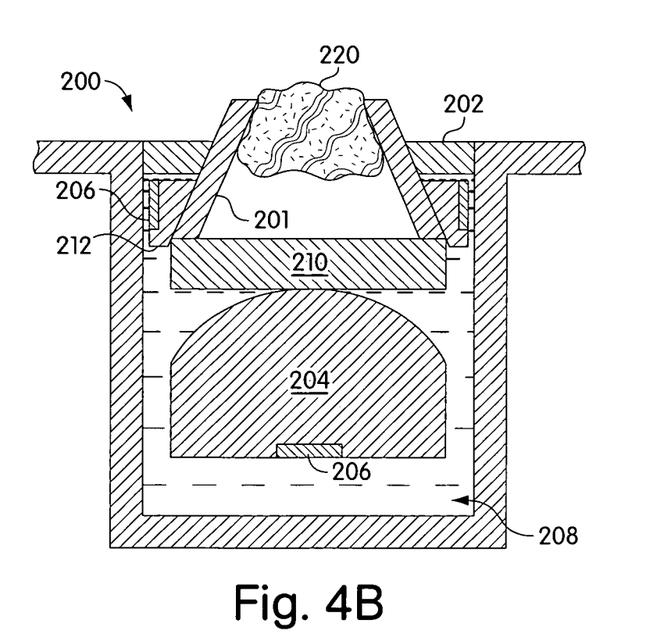
FIG. 4B is a diagram of the sampling device of FIG. 4A deployed to take a sample in one embodiment of the invention.
Figure 4C:
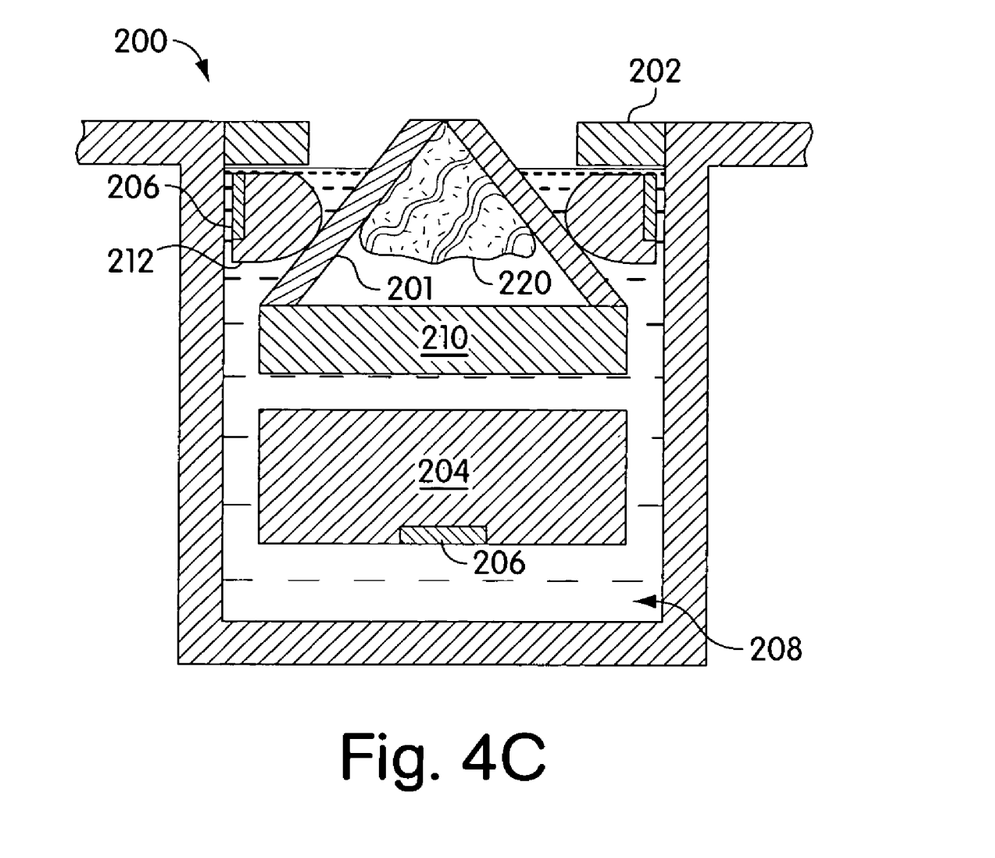
FIG. 4C is a diagram of the sampling device of FIGS. 4A and 4B in a position after deployment in one embodiment of the invention.

The sampling devices are one of vacuum sampling devices, mechanical cutting sampling devices, and deployed sampling devices, each of which is suitable in an array pattern on a catheter 50. A combination of sampling devices 54 is also effective for the removal of multiple samples. Referring to FIGS. 2-4, three embodiments of the sampling devices of the invention are shown. The sampling devices are embedded into the catheter shown in FIG. 1 using micromachining technologies that are used, for example, in the production of polymer micromachines on Kapton substrates. Numerous micromachining technologies are used for the fabrication of polymer micromachines, including casting, molding, and thin film etching. Each of these technologies is used to produce medical instrumentation having sampling devices positioned on an outer diameter of the instrumentation, generally on a shaft portion.

In addition, the sampling devices 54 are fabricated with biodegradable polymers. The use of biodegradable polymers allows implementations of this invention with portions that deliberately break off during use, are left within the body, and cause no harm, as they are broken down and absorbed within the body. The sampling devices 54 need not be fabricated with biodegradable materials; however, use of biodegradable materials removes the danger associated with portions that break or fail during use.

Vacuum Sampling Device

Referring to FIG. 2, an embodiment of a sampling device used in the catheter of FIG. 1 is illustrated in the form of a vacuum sampling device. The vacuum sampling system 10 includes a chamber 3, a covering material 2 and a bonding material 1. The chamber 3 is enclosed on one side by the covering material 2. The covering material 2 is bonded by the bonding material 1 on a surface of the covering material 2 that faces an interior of the chamber 3. The chamber 3 is manufactured out of an appropriate material, such as a MEMS material, including but not limited to, silicon, a polymer such as PDMS or biodegradable polymer, or a metal or metal alloy such as nickel or nickel alloy. The covering material 2 is a polymer. The bonding material 1 is a conductive polymer or a metal, including, but not limited to gold. The bonding material 1 can be other materials that lose strength when heated. Other suitable materials are also within the scope of the invention.

The chamber 3 is covered with the covering material 2 while under vacuum. Alternatively, the chamber 3 is covered and then a vacuum is drawn on the chamber 3. The covering material 2 separates into two respective parts when the bonding material 1 is removed, causing the two sides of the covering material 2 to separate due to the differential pressure across the material. The bonding material 1 is removed or equivalently weakened so that it no longer holds the covering material 2 in place. The bonding material is eliminated in order to collect the tissue or fluid sample into the chamber 3. Weakening of the bonding material 1 is accomplished by passing a small current through the bonding material 1, such as heating the bonding material via ohmic heating, which causes it to increase in temperature and therefore lose its strength. For example, thin film deposition technologies, such as those used in flexible circuits, deposit conductive vias that provide electrical power to each of the sampling devices. The conductive vias, or ducts, are positioned on an outside surface of the catheter, rather than inside the catheter body. At a lower strength, the bonding material 1 does not hold the cover in place due to the differential pressure on each side of the cover, and the cover opens. The internal vacuum then draws either tissue or fluid from the exterior of the chamber 3 into the chamber 3. The differential pressure is equalized as material fills the chamber 3, the chamber 3 having been previously under vacuum. Once the pressure is equalized, the covering material 2 closes, sealing the chamber 3 and holding and isolating a volume of either a fluid or tissue sample. The sample is not transported to a different location on the catheter, but is contained in the chamber on the outer diameter of the catheter.

Vacuum sampling is also achieved through the withdrawal of a piston into the sampling chamber or application of a vacuum to the chamber using microvalves and either an external vacuum pump or vacuum reservoir. The covering material 2 in FIG. 2 is contoured to provide tight closure once pressure is equalized on either side of the material. The covering material 2 can also be contoured to cut through material drawn into the cavity under vacuum, also isolating the tissue. The covering material is designed to separate using an electrical, fluid or other signal without requiring a bonding material. For example, the covering material is made conductive in a region where separation is desired. An electrical current is sent through the conducting region, causing it to heat, lose strength, and subsequently separate.

An additional embodiment of the vacuum sampling device of FIG. 2 includes a single flap configuration, where the flap separates next to a side of the chamber 3 and rotates against an opposite chamber wall subsequent to removal of the bonding material 1. The resulting cavity of the chamber 3 is closed by a blade that both cuts the tissue that is then contained in the chamber 3 and seals the chamber 3.

The configuration illustrated in FIG. 2 is replicated using micromachining technology to produce many such chambers on either a contoured substrate or on a flexible substrate that can be placed over a catheter end. Volumes of such sampling chambers range from as small as about a picoliter or less and as large as about a few hundred microliters or more. The chambers are fabricated by molding a polymer over a contoured mold, or by etching a cavity into a substrate, such as silicon, using micromachining. Other suitable methods can be employed, alternatively or additionally.

Mechanical Cutting Sampling Device

Rapid sampling can be accomplished using additional methods and apparatus. Referring to FIG. 3, a sampling device using mechanical cutting is depicted. The mechanical cutting devices are places along the length of the catheter, preferably on an outside diameter. A small, sharp, and contoured shape cuts tissue or scoops out tissue when the external surface of the biopsy device is placed against the tissue. The shape of the cutting device is in the form of a curved three-dimensional shape or a flat blade. Preferably, the mechanical cutting device is scoop-shaped and both cuts tissue that is drawn into a cavity and subsequently seals that cavity by the nature of the shape and motion of the cutting device.

Referring to FIG. 3, the mechanical cutting device 100 includes a substrate 6, a curved three-dimensional scoop 7, a pivot 8, and an edge 9. The substrate 6 holds the curved three-dimensional scoop 7 that rotates around the preloaded pivot 8. The curved shape edge 9 is of sufficient sharpness to cut through tissue and carry the tissue with the scoop as it rotates clockwise in the direction of arrow 12 and comes to rest against the substrate in a rest position 10. A tissue 5 is then held in position by the scoop 7 that is loaded against the substrate 6. The scoop is sufficiently large to obtain the required amount of tissue, i.e., less than a cubic millimeter, and can be a volume one hundred times smaller than a cubic millimeter.

The substrate 6 and scoop 7 may be fabricated of any appropriate material. For example, the substrate 6 is fabricated from a number of suitable materials, including but not limited to a ceramic, metallic, or polymeric composition. The preloaded three-dimensional scoop 7 is fabricated from a number of suitable materials, including but not limited to a ceramic, metallic, or polymeric composition. The pivot 8 is a torsional shaft that is preloaded into its cavity by moving the scoop 7 manually into the cavity and applying a heat sensitive, conductive bonding material. The scoop 7 is released by applying a current to the bonding material. The current applied to the bonding material releases the scoop 7 and captures a tissue sample 5. Again, conductive vias can be deposited to provide electrical power to each of the sampling devices. Actuation technologies for the pivot 8 include stored mechanical energy released by a heat or electrically actuated latching device. The electrical ducts or wires used to provide heat to actuate the device can be located on an outside surface of the catheter, rather than on an inside tunnel of the catheter. Other embodiments of the invention include additional actuation technologies such as, for example, shape memory alloys.

Again, the sample is advantageously contained in the scoop at the locale in which the sample is acquired. The sample is not transported, but is kept isolated until the catheter is removed from the subject.

Deployed Sampling Device

A further embodiment of the invention is a sampling device that includes a miniature set of jaws that deploys from a chamber, seizes a portion of tissue and withdraws into the chamber to retain the tissue sample. Referring to FIGS. 4A, 4B, and 4C, a deployed sampling device is shown. A deployed sampling device 200 includes a set of sampling jaws 201, a cover 202, an expandable volume 204, a heating element 206, a chamber 208, an actuation piston 210, and a filled chamber 212. The chamber encloses the sampling jaws 201, the cover 202, the expandable volume 204, the heating element 206, the filled chamber 212 and the actuation piston 210. The jaws 201 are positioned in an upper portion of the chamber 208, above the position of the actuation piston 210. The actuation piston 210 is positioned above the expandable volume 204, and the expandable volume contains the heating element 206. The filled chamber 212 further includes a second heating element, and is positioned in a top side portion of the chamber 208.

Referring to FIG. 4B, the expandable volume 204 can be expanded by heating a fluid within the chamber 208 with the heating element 206, causing the jaws 201 to extend from the chamber 208, penetrating through the cover 202 and surrounding a tissue sample 220. The expandable volume is either air that is heated or liquid that is pressurized by a central lumen in the catheter connected to each of the deploying sampling devices 200. The expandable volume can be heated electrically, and the electrical wires are positioned on an outside surface of the catheter, obviating the need to have an inner lumen. The expandable volume 204 can be a fraction of a cubic millimeter, for example, from 0.001 to 1 cubic millimeter.

A second, annular, filled chamber 212 with a heating element 206, substantially the same as the heating element 206 in the chamber, then expands to close the jaws 201 and causes them to retract, holding the tissue sample 220 for subsequent examination, as shown in FIG. 4C. The filled chamber 212 causes pressure to be placed on an outside surface of the extended jaws, such that the jaws return to a position within the chamber. A filled chamber 212 is positioned such that contact is made with each of the jaws 201. Alternatively, the jaws 201, by design, naturally sit within the cavity 208, and are deployed by an internal pressure within the expandable volume 204. When the pressure within the volume decreases, for example by cooling, the jaws 201 retract back within the chamber 208 holding a tissue sample 220. Other embodiments of the invention include additional methods of retracting the jaws into the chamber.

The sample is contained in the jaws 201 within the chamber 212 for the duration of sampling and until the catheter is removed from the subject. Other devices that are deployed from a position along the diameter of the catheter are envisioned and effectively draw a sample into the chamber for containment.

Further Embodiments of the Invention

Embodiments of the invention describe individual sampling techniques and devices wherein mechanisms for collecting samples of tissue or fluids are activated, generally by heat or electricity. Samples are collected upon insertion of a catheter having a plurality of sampling devices along its length. In certain embodiments of the invention, sampling devices can be placed in a linear array along a biopsy device and then deployed simultaneously to map the variation of tissue in a given line or direction. Multiple linear samples can be taken to evaluate the extent of change of tissue characteristics, for example, the extent of tumor growth. The catheter is a solid body having the sampling devices positioned, or essentially carved out, of its diameter. Wires and other electrical devices are attached on the outside surface of the catheter, rather than in an inner lumen.

In still further embodiments of the invention, sampling devices can also be placed on a movable platform that places the sampling devices at the same location, such as the tip, on the larger insertion apparatus or platform, such as a catheter. This movable platform can be a flexible plastic belt that can be translated around a catheter sampling tip. This permits the operator of the insertion apparatus or platform to position the sampling devices at the same point of the insertion apparatus or platform each time.

In still further embodiments of the invention, the catheter sampling tip can hold an array of sampling devices on the same surface depending on the size of the catheter sampling tip and the sampling devices. An operator of the biopsy or sampling apparatus or platform can then take multiple samples at effectively the same position on the apparatus or platform. One advantage of this embodiment allows for the removal of the need to know where on the sampling apparatus or platform the sample was taken.

The miniaturization of the sampling device permits the addition of fiberoptic imaging to view the actual sampling location, as well as capturing visual images of each sampling site. Sampling devices, for example, can be located around a central fiber optic imaging lens.

Devices according to the invention also provide for discharge of the fluid and/or tissue samples when the catheter has been removed from the subject being tested. For example, the vacuum sampling devices permit ejection of samples by pressurization of the chamber or by drawing a vacuum across the chamber. Also, for example, the cutting sample devices can be reversed mechanically. Moreover, the deployed sampling devices can release the sample by re-pressurizing the deployment volume to re-deploy the sampling jaws.

In certain embodiments, devices according to the invention reduce the amount of cross contamination of samples. The samples are individually contained in the respective chambers of the sampling devices. This increases the assurance that a given sample removed from a specific sampling device is uncontaminated by other samples.

In other embodiments, devices according to the invention permit an application of drug delivery. For example, vacuum sampling devices can be reversed by including a frangible or separating membrane that can separate under pressure, ejecting internal contents. The advantages of this embodiment include, for example, providing sufficient pressure to more effectively penetrate any coating formed on the surfaces as well as provide a more vigorous release of medication. Applications of this embodiment include placing, for example, these drug delivery structures on catheters to provide measured release of marking fluid or medications that require very accurate placement. In addition, multiple drugs can be included on the same device, permitting simple and rapid, situation-dependent, delivery of medication.

In other embodiments, a sampling device can be implemented in a standalone version. For example, the sampling device can be implanted or swallowed, and samples may be taken at defined time periods. As a result, body or digestive system chemistry or environments can be sampled over time. The standalone product can have a small internal powered control circuit that defines the time spacing or cycle of the different sampling events. Alternatively, in other embodiments, sampling devices can have dissolvable or passive, unpowered actuation that actuate at different times without requiring a source of internal energy or power. Drug kinetics can be monitored, digestive systems evaluated, and various physiological quantities can be monitored. Such an invention provides previously unavailable diagnostic information or information that would be difficult to collect and/or be particularly uncomfortable to the patient otherwise.

The invention can be embodied in other specific forms without departing from the spirit or essential characteristics thereof. The foregoing embodiments are, therefore, to be considered in all respects illustrative rather than limiting on the invention described herein.

Having thus described at least one illustrative embodiment of the invention, various alterations, modifications and improvements will readily occur to those skilled in the art. Such alterations, modifications and improvements are intended to be within the scope and spirit of the invention. Accordingly, the foregoing description is by way of example only and is not intended as limiting. The invention's limit is defined only in the following claims and the equivalents thereto.

What is claimed is:

1. A method of extracting multiple tissue samples from a subject, comprising inserting into a volume of a tissue an instrument comprising a sharp distal end and a plurality of controllable tissue sampling devices each of said devices being located in a different position in an array along a longitudinal axis of a housing and a plurality of isolated chambers, each of said sampling devices comprising a corresponding one of said isolated chambers, the volume of each of said isolated chambers being less than 1.2 cubic millimeters;

actuating at least one of said a sampling devices by a deployment signal, said signal being selected from the group consisting of an electrical, optical, pneumatic, hydraulic, RF-transmitted, inductive, magnetic, thermal or sonic signal, said signal causing an opening of said chamber;

removing tissue samples from anatomical locations at varying depths within said tissue; and sealing said chamber.

2. The method of claim 1, wherein said sampling devices are deployed simultaneously.

3. The method of claim 1, wherein each of said sampling devices is deployed temporally.

4. The method of claim 1, wherein the volume of each of said isolated chambers is selected from the group consisting of 0.005, 0.01, 0.05, 0.1, 0.5, and 0.75 cubic millimeters.

5. The method of claim 1, wherein said instrument comprises greater than 50 of said isolated chambers.

6. The method of claim 1, wherein said tissue sampling devices remove samples at varying depths in said tissue to map variation in a given line or direction.

7. The method of claim 1, wherein said tissue comprises a diseased area.

8. The method of claim 1, wherein said tissue comprises a tumor.

9. The method of claim 8, wherein multiple linear samples are taken to evaluate the extent of tumor growth.

10. The method of claim 1, wherein multiple linear samples are taken to evaluate the extent of change of tissue characteristics.

11. A method of extracting multiple tissue samples from a subject, the method comprising:

inserting into a volume of a tissue an instrument comprising a sharp distal end, a plurality of controllable tissue sampling devices each of said devices being located in a different position in an array along a longitudinal axis of a housing, and a plurality of isolated chambers each of said sampling devices comprising a corresponding one of said isolated chambers, the volume of said isolated chamber being less than 1.2 cubic millimeters;

heating the plurality of sampling devices, heating causing actuation of a mechanical portion of the plurality of sampling devices, such that a mechanical portion of the sampling devices collects samples from varying depths within said tissue and retains the samples;

depositing the samples into said isolated chambers; and removing the instrument from the subject.

12. The method of claim 11, wherein heating comprises passing electrical current through a portion of the sampling device.

13. The method of claim 11, wherein collecting and retaining the sample comprises applying a differential pressure to at least one of said isolated chambers and sucking the sample into the isolated chamber.

14. The method of claim 11, further comprising ejecting the samples by pressurizing the chamber.

15. The method of claim 11, wherein collecting and retaining the sample comprises scooping the sample from the subject by pivoting a scoop from a rest position after heating the scoop.

16. The method of claim 11, wherein collecting and retaining the sample comprises expanding a volume of a fluid in a chamber and causing a set of jaws to deploy from the chamber.

17. The method of claim 11, further comprising imaging a location of the sample fiberoptically.

18. The method of claim 11, wherein the volume of each of said isolated chambers is selected from the group consisting of 0.005, 0.01, 0.05, 0.1, 0.5, and 0.75 cubic millimeters.

19. The method of claim 11, wherein said instrument comprises greater than 50 of said isolated chambers.

20. The method of claim 11, wherein said tissue sampling devices remove samples at varying depths in said tissue to map variation in a given line or direction.

21. The method of claim 11, wherein said tissue comprises a diseased area.

22. The method of claim 11, wherein said tissue comprises a tumor.

23. The method of claim 22, wherein multiple linear samples are taken to evaluate the extent of tumor growth.

24. The method of claim 11, wherein multiple linear samples are taken to evaluate the extent of change of tissue characteristics.

* * * * *